US011285185B2

(12) United States Patent
Saurat et al.

(10) Patent No.: US 11,285,185 B2
(45) Date of Patent: *Mar. 29, 2022

(54) **METHODS FOR TREATING IN DERMATOLOGY AND DERMO-COSMETICS BY ADMINISTERING *SILYBUM MARIANUM* ACHENE EXTRACT**

(71) Applicant: PIERRE FABRE DERMO-COSMETIQUE, Boulogne-Billancourt (FR)

(72) Inventors: Jean-Hilaire Saurat, Geneva (CH); Olivier Sorg, Geneva (CH); Mathieu Leti, Montgiscard (FR); Bernard Fabre, Belberaud (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 292 days.

This patent is subject to a terminal disclaimer.

(21) Appl. No.: 16/313,835

(22) PCT Filed: Jun. 30, 2017

(86) PCT No.: PCT/EP2017/066349
§ 371 (c)(1),
(2) Date: Dec. 27, 2018

(87) PCT Pub. No.: WO2018/002338
PCT Pub. Date: Jan. 4, 2018

(65) Prior Publication Data
US 2019/0175677 A1   Jun. 13, 2019

(30) Foreign Application Priority Data
Jul. 1, 2016   (FR) ...................... 1656328

(51) Int. Cl.
| | | |
|---|---|---|
| *A61K 36/28* | (2006.01) | |
| *A61K 9/00* | (2006.01) | |
| *A61K 47/10* | (2017.01) | |
| *A61Q 19/00* | (2006.01) | |
| *A61K 8/9789* | (2017.01) | |
| *A61K 9/10* | (2006.01) | |
| *A61P 17/10* | (2006.01) | |
| *A61P 17/08* | (2006.01) | |
| *A61K 31/201* | (2006.01) | |
| *A61K 31/35* | (2006.01) | |
| *A61K 31/355* | (2006.01) | |
| *A61K 31/357* | (2006.01) | |
| *A61K 31/56* | (2006.01) | |
| *A61K 31/575* | (2006.01) | |

(52) U.S. Cl.
CPC ............ *A61K 36/28* (2013.01); *A61K 8/9789* (2017.08); *A61K 9/0014* (2013.01); *A61K 9/10* (2013.01); *A61K 31/201* (2013.01); *A61K 31/35* (2013.01); *A61K 31/355* (2013.01); *A61K 31/357* (2013.01); *A61K 31/56* (2013.01); *A61K 31/575* (2013.01); *A61K 47/10* (2013.01); *A61P 17/08* (2018.01); *A61P 17/10* (2018.01); *A61Q 19/00* (2013.01); *A61Q 19/008* (2013.01); *A61K 2236/00* (2013.01); *A61K 2236/17* (2013.01); *A61K 2236/33* (2013.01); *A61K 2236/331* (2013.01)

(58) Field of Classification Search
CPC .............................. A61K 36/26; A61K 36/889
USPC .................................................. 424/764, 727
See application file for complete search history.

(56) References Cited

U.S. PATENT DOCUMENTS

| | | | |
|---|---|---|---|
| 8,980,344 B2 * | 3/2015 | Gross ................... | A61K 8/4953 424/777 |
| 2007/0059269 A1 * | 3/2007 | Bernard ................. | A61K 8/362 424/70.22 |
| 2013/0323228 A1 | 12/2013 | Norman | |

FOREIGN PATENT DOCUMENTS

| | | | |
|---|---|---|---|
| CN | 104673486 A | 6/2015 | |
| EP | 0552439 A1 * | 7/1993 | ............. A61K 36/28 |
| GB | 2084569 A | 4/1982 | |
| JP | 2000/169332 A | 6/2000 | |

OTHER PUBLICATIONS

Andrzejewska et al., "Silybum Marianum: Non-medical Exploitation of the Species", Annals of Applied Biology, vol. 167, 2015, (published online Jun. 18, 2015), pp. 285-297 (Total 14 pages).
Barreto, "Extraction of Silymarin Compounds From Milk Thistle (*Silybum marianum*) Seed Using Hot, Liquid Water as the Solvent", Agricultural, Biological and Chemical Engineering, vol. 3, 2002, pp. 91-97.
Berardesca et al., "Combined Effects of Silymarin and Methylsulfonylmethane in the Management of Rosacea: Clinical and Instrumental Evaluation", Journal of Cosmetic Dermatology, vol. 7, Sep. 27, 2007, pp. 8-14.
Hermenean et al., "Antioxidant and Hepatoprotective Activity of Milk Thistle (*Silybum marianum* L. Gaertn.) Seed Oil", Open Life Sci, vol. 10, 2015, pp. 225-236.

(Continued)

Primary Examiner — Ralph J Gitomer
(74) Attorney, Agent, or Firm — Birch, Stewart, Kolasch & Birch, LLP

(57) ABSTRACT

The present invention relates to a *Silybum marianum* (L.) Gaertn. extract comprising less than 0.2% by weight of silymarin with respect to the weight of the dry extract, as well as pharmaceutical and cosmetic compositions containing same, the preparation method thereof and uses thereof as a medicinal product, particularly in the treatment of acne, seborrhoea, seborrheic dermatitis and/or rosacea.

15 Claims, 9 Drawing Sheets

(56) References Cited

OTHER PUBLICATIONS

International Search Report for International Application No. PCT/EP2017/066349 dated Aug. 11, 2017.

Kuki et al., "Identification of Silymarin Constituents: An Improved HPLC-MS Method", Chromatographia, vol. 75, 2012 (published online Nov. 20, 2011, pp. 175-180.

Prescha et al., "The Antioxidant Activity and Oxidative Stability of Cold-Pressed Oils", J. Am. Oil Chem. Soc., vol. 91, 2014 (published online May 16, 2014), pp. 1291-1301.

Sahib et al., "Effects of Oral Antioxidants on Lesion Counts Associated With Oxidative Stress and Inflammation in Patients With Papulopustular Acne", Journal of Clinical and Experimental Dermatology Research, vol. 3, Issue 5, 2012, pp. 1-6.

Unknown, "Guidance for Industry Acne Vulgaris: Developing Drugs for Treatment", U.S. Department of Health and Human Services Food and Drug Administration Center for Drug Evaluation and Research (CDER), Sep. 2015, pp. 1-14 (Total 17 pages).

Wilkin et al. "Standard Grading System for Rosacea: Report of the National Rosacea Society Expert Committee on the Classification and Staging of Rosacea", J. Am. Acad. Dermatol., vol. 50, 2004, pp. 907-912.

Wynne et. al., "Value-adding Factors in Cold-pressed Edible Seed Oils and Flours", Food Science, 2006, pp. 1-143 (Total 154 pages).

Zheng et al., "Application of Response Surface Methodology to Optimize Microwave-assisted Extraction of Silymarin From Milk Thistle Seeds", Separation and Purification Technology, vol. 70, 2009, pp. 34-40.

Zhu et al., "Silybum Marianum Oil Attenuates Oxidative Stress and Ameliorates Mitochondrial Dysfunction in Mice Treated With D-Galactose", Pharmacogn Mag, vol. 10 (Suppl 1), S92-S99, 2014, pp. 1-18.

* cited by examiner

METHODS FOR TREATING IN DERMATOLOGY AND DERMO-COSMETICS BY ADMINISTERING *SILYBUM MARIANUM* ACHENE EXTRACT

FIELD OF THE INVENTION

The present invention relates to a novel *Silybum marianum* (L.) Gaertn. achene extract, as well as pharmaceutical and cosmetic compositions containing same intended more particularly for topical application, the preparation method thereof and uses thereof in dermatology or cosmetology, particularly in the treatment of acne, seborrhoea, seborrheic dermatitis and/or rosacea.

STATE OF THE RELATED ART

The scientific name *Silybum marianum* (L.) Gaertn. denotes a plant belonging to the Asteraceae family, that is annual or biannual with a robust stem than can reach up to one metre in height. Its large, shiny, alternate leaves devoid of stipules are mottled with white and surrounded by hard, sharp thorns. The flowers are clustered in flower heads, frequently solitary. They are surrounded by large spiny bracts with very sharp ends. The flowers with tubules and five lobes are violet purple in colour. The fruits are shiny, black or yellow-mottled achenes, topped with a pappus with denticulate bristles arranged in a ring at the base thereof. The vernacular name of this plant is milk thistle.

The achene (frequently incorrectly referred to as seed in the literature) of *Silybum marianum* (L.) Gaertn. and the preparations thereof are traditionally used orally, in the symptomatic treatment of digestive function disorders attributed to the liver in origin.

The main active ingredient of the achene of *Silybum marianum* (L.) Gaertn. is silymarin, a mixture of a plurality of flavonolignans (essentially silybin, isosilybin, silychristin and silydianin). The achenes contain up to 3% by weight of silymarin. They also consist of oil (20-30% by weight), mucilage and proteins.

Silymarin has been the subject of numerous studies (in vitro, in vivo and clinical) having demonstrated the antioxidant, hepatoprotective, digestive, or anti-inflammatory properties thereof.

At the present time, *Silybum marianum* (L.) Gaertn. achene extracts high in silymarin are present in a plurality of pharmaceutical preparations intended for treating various liver and bile disorders, such as Legalon®.

Moreover, silymarin has been the subject of a study in the treatment of acne (Sahib et al. 2012), as well as in the treatment of erythematoteleangiectatic rosacea in association with methylsulphonylmethane (MSM) (Berardesca et al. 2008).

*Silybum marianum* (L.) Gaertn. oil, rich in omega 6 and in vitamin E, is essentially used in cooking. It is obtained conventionally from achenes by cold pressing.

Studies on the antioxidant and hepatoprotective properties of such a milk thistle oil, administered orally, have however been conducted in vivo on rats or mice (Hermenean et al. 2015; Zhu et al. 2014).

SUMMARY OF THE INVENTION

The Applicant demonstrated surprisingly that a *Silybum marianum* (L.) Gaertn. achene extract low in silymarin exhibited very interesting properties for the treatment of acne, seborrhoea, rosacea or seborrheic dermatitis.

One subject-matter of the invention therefore relates to a *Silybum marianum* (L.) Gaertn. achene extract comprising less than 0.2%, preferably less than 0.1% by weight of silymarin with respect to the weight of the dry extract for use thereof in the treatment of acne, seborrhoea, rosacea and/or seborrheic dermatitis.

A further subject-matter of the invention relates to the use of a *Silybum marianum* (L.) Gaertn. achene extract comprising less than 0.2%, preferably less than 0.1% by weight of silymarin with respect to the weight of the dry extract for the manufacture of a medicinal product intended for the treatment of acne, seborrhoea, rosacea and/or seborrheic dermatitis.

A further subject-matter of the invention relates to the use of a *Silybum marianum* (L.) Gaertn. comprising less than 0.2%, preferably less than 0.1% by weight of silymarin with respect to the weight of the dry extract in the treatment of acne, seborrhoea, rosacea and/or seborrheic dermatitis.

A further subject-matter of the invention relates to a method for the treatment of acne, seborrhoea, rosacea and/or seborrheic dermatitis comprising the administration to a subject in need thereof of an effective quantity of a *Silybum marianum* (L.) Gaertn. achene extract comprising less than 0.2%, preferably less than 0.1% by weight of silymarin with respect to the weight of the dry extract.

A further subject-matter of the invention relates to a *Silybum marianum* (L.) Gaertn. achene extract comprising less than 0.2%, preferably less than 0.1% by weight of silymarin with respect to the weight of the dry extract.

A further subject-matter of the invention relates to a *Silybum marianum* (L.) Gaertn. achene extract comprising less than 0.2%, preferably less than 0.1% by weight of silymarin with respect to the weight of the dry extract for use thereof as a medicinal product.

A further subject-matter of the invention relates to a pharmaceutical (particularly dermatological) or cosmetic (particularly dermo-cosmetic) composition comprising a *Silybum marianum* (L.) Gaertn. achene extract comprising less than 0.2%, preferably less than 0.1% by weight of silymarin with respect to the weight of the dry extract in a mixture with at least one pharmaceutically or cosmetically acceptable excipient.

A further subject-matter of the invention relates to a pharmaceutical (particularly dermatological) or cosmetic (particularly dermo-cosmetic) composition comprising a *Silybum marianum* (L.) Gaertn. achene extract comprising less than 0.2%, preferably less than 0.1% by weight of silymarin with respect to the weight of the dry extract in a mixture with at least one pharmaceutically or cosmetically acceptable excipient for use thereof in the treatment of acne, seborrhoea, rosacea and/or seborrheic dermatitis.

A further subject-matter of the invention relates to the use of a pharmaceutical (particularly dermatological) or cosmetic (particularly dermo-cosmetic) composition comprising a *Silybum marianum* (L.) Gaertn. achene extract comprising less than 0.2%, preferably less than 0.1% by weight of silymarin with respect to the weight of the dry extract in a mixture with at least one pharmaceutically or cosmetically acceptable excipient in the treatment of acne, seborrhoea, rosacea and/or seborrheic dermatitis.

A further subject-matter of the invention relates to a method for the treatment of acne, seborrhoea, rosacea and/or seborrheic dermatitis comprising the administration, preferably by the topical route, to a subject in need thereof of an effective quantity of a pharmaceutical (particularly dermatological) or cosmetic (particularly dermo-cosmetic) composition comprising a *Silybum marianum* (L.) Gaertn.

achene extract comprising less than 0.2%, preferably less than 0.1% by weight of silymarin with respect to the weight of the dry extract in a mixture with at least one pharmaceutically or cosmetically acceptable excipient.

A further subject-matter of the invention relates to a method for preparing a *Silybum marianum* (L.) Gaertn. achene extract comprising less than 0.2%, preferably less than 0.1% by weight of silymarin with respect to the weight of the dry extract comprising a step for extracting an oil obtained from *Silybum marianum* (L.) Gaertn. achenes with an extraction solvent comprising, particularly consisting of, a hydrotropic aqueous solution, subcritical water or an organic solvent not miscible with the oil obtained from *Silybum marianum* (L.) Gaertn. achenes optionally in a mixture with water.

DETAILED DESCRIPTION

In the present description, the *Silybum marianum* (L.) Gaertn. plant may be referred to using the abbreviated term *Silybum marianum*.

The term "silymarin" denotes according to the present invention a purified *Silybum marianum* (L.) Gaertn. achene extract comprising mostly (at least 95% by weight) a mixture of the following four flavonolignans: silybin, isosilybin, silychristin and silydianin (Kuki et al. 2012). A silymarin content less than 0.2% by weight thereof means that the total quantity of constituents of silymarin is less than 0.2% by weight. Such a content may be determined particularly by HPLC (high-performance liquid chromatography) or UPLC (ultra-high-performance liquid chromatography) by calculating the total area of the peaks corresponding to all the constituents of silymarin, particularly using a reference silymarin sample, which can be obtained for example from Sigma Aldrich, to determine the position of these peaks.

The term "silybin", also referred to as silibinin in the art, denotes, according to the present invention, the four diastereoisomers silybin A, silybin B, 2,3-cis-silybin A and 2,3-cis-silybin B.

The term "isosilybin" denotes, according to the present invention, the two diastereoisomers isosilybin A and isosilybin B.

The term "silychristin" denotes, according to the present invention, the two diastereoisomers silychristin A and silychristin B.

The term "approximately" denotes in the present description that the value in question can be less or greater by 10%, particularly 5%, in particular 1%, than the value indicated. The term "dry extract" denotes, according to the present invention, an extract devoid of extraction solvent or merely containing same at non-significant trace levels. Such a dry extract thus contains only matter obtained from *Silybum marianum* (L.) Gaertn. It may also contain non-significant traces of extraction solvent.

The term "organic solvent not miscible with the oil obtained from *Silybum marianum* (L.) Gaertn. achenes" denotes, according to the present invention, an organic solvent which is not capable of mixing, or merely partially, with the oil obtained from *Silybum marianum* (L.) Gaertn. alkenes, such that the mixture of organic solvents and oil obtained from *Silybum marianum* (L.) Gaertn. achenes produces a heterogeneous mixture wherein at least two separate phases can be observed.

Extract According to the Invention

The extract according to the invention is a *Silybum marianum* achene extract comprising less than 0.2%, preferably less than 0.1% by weight of silymarin with respect to the weight of the dry extract.

According to one particular embodiment, the extract according to the invention contains at least 0.5% by weight, preferably at least 1.0% by weight of beta-sitosterol with respect to the dry extract. In particular, the extract according to the invention contains between 0.5% and 2.5% by weight, particularly between 1.0% and 2.0% by weight, for example approximately 1.5% by weight of beta-sitosterol with respect to the weight of the dry extract. The mass ratio of silymarin/beta-sitosterol of the extract according to the invention may be in particular less than 0.4, particularly less than 0.07. The extract according to the invention may further comprise between 2 and 7% by weight, particularly between 3 and 6% by weight, for example between 3 and 5% by weight of sterols with respect to the weight of the dry extract.

The term "sterol" denotes, according to the present invention, a molecule having a sterane nucleus wherein the carbon 3 carries a hydroxyl group OH, the sterane having the following structure:

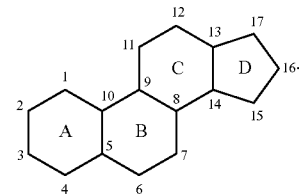

According to one particular embodiment, the extract according to the invention contains at least 3% by weight, preferably at least 4% by weight of free linoleic acid with respect to the weight of the dry extract. In particular, the extract according to the invention contains between 3% and 15% by weight, particularly between 4% and 10% by weight, in particular between 4% and 6% by weight, for example approximately 5% by weight of free linoleic acid with respect to the weight of the dry extract. The extract according to the invention may further comprise between 10% and 70%, in particular between 10% and 30% by weight, particularly between 15% and 25% by weight of free fatty acids with respect to the weight of the dry extract.

The term "fatty acid" denotes, according to the present invention, a carboxylic acid $R1CO_2H$ wherein the chain $R1$ is a linear or branched hydrocarbon chain, saturated or comprising double C=C bonds, the carboxylic acid comprising 16 to 22 carbon atoms (including the carbon atom of the carboxylic acid function).

The term "free" fatty acid (including linoleic acid) denotes, according to the present invention, a fatty acid not bound to other molecules (e.g. to glycerol or derivatives thereof to produce glycerides or to an alcohol to produce a fatty ester).

According to a further particular embodiment, the extract according to the invention contains between 0.5% and 2.5% by weight, particularly between 1.0% and 2.0% by weight, for example approximately 1.5% by weight of beta-sitosterol with respect to the weight of the dry extract and between 3% and 15% by weight, particularly between 4% and 10% by weight, in particular between 4% and 6% by weight, for example approximately 5% by weight of free linoleic acid with respect to the weight of the dry extract. The mass ratio of silymarin/beta-sitosterol of the extract according to the invention may be in particular less than 0.4, particularly less than 0.07. The extract according to the invention may further comprise between 2 and 7% by weight, particularly between 3 and 6% by weight, for example between 3 and 5% by weight of sterols with respect to the weight of the dry extract and between 10% and 50%, in particular between 10% and 30% by weight, particularly between 15% and 25% by weight of free fatty acids with respect to the weight of the dry extract.

According to one particular embodiment, the extract according to the invention contains at least 0.01% by weight, particularly at least 0.05% by weight of tocopherols with respect to the weight of the dry extract. In particular, the extract according to the invention contains between 0.01% and 0.5% by weight, particularly between 0.05% and 0.2% by weight, for example approximately 0.1% by weight of tocopherols with respect to the weight of the dry extract. The mass ratio of silymarin/tocopherols of the extract according to the invention may be in particular less than 1, particularly less than 0.1.

The term "tocopherol" denotes, according to the present invention, α-tocopherol, β-tocopherol, γ-tocopherol and δ-tocopherol.

According to a further particular embodiment, the extract according to the invention contains between 0.5% and 2.5% by weight, particularly between 1.0% and 2.0% by weight, for example approximately 1.5% by weight of beta-sitosterol with respect to the weight of the dry extract; between 3% and 15% by weight, particularly between 4% and 10% by weight, in particular between 4% and 6% by weight, for example approximately 5% by weight of free linoleic acid with respect to the weight of the dry extract; and between 0.01% and 0.5% by weight, particularly between 0.05% and 0.2% by weight, for example approximately 0.1% by weight of tocopherols with respect to the weight of the dry extract. The extract according to the invention may further comprise between 2 and 7% by weight, particularly between 3 and 6% by weight, for example between 3 and 5% by weight of sterols with respect to the weight of the dry extract and between 10% and 50%, in particular between 10% and 30% by weight, particularly between 15% and 25% by weight of free fatty acids with respect to the weight of the dry extract. The mass ratio of silymarin/beta-sitosterol of the extract according to the invention may be in particular less than 0.4, particularly less than 0.07. The mass ratio of silymarin/tocopherols of the extract according to the invention may be in particular less than 1, particularly less than 0.1.

Preferably, the extract according to the present invention will be a dry extract.

According to a preferred embodiment, the extract according to the invention is suitable for being obtained by means of a method according to the invention described hereinafter.

Method for Preparing the Extract According to the Invention

A method for preparing an extract according to the invention comprises a step for extracting an oil obtained from *Silybum marianum* (L.) Gaertn. achenes with an extraction solvent comprising, particularly consisting of, a hydrotropic aqueous solution, subcritical water or an organic solvent not miscible with the oil obtained from *Silybum marianum* (L.) Gaertn. achenes optionally in a mixture with water.

According to one particular embodiment, the organic solvent comprises, particularly consists of, an organic solvent not miscible with the oil obtained from *Silybum marianum* (L.) Gaertn. achenes optionally in a mixture with water.

The organic solvent not miscible with the oil obtained from *Silybum marianum* (L.) Gaertn. achenes may be particularly a $C_1$ to $C_3$ alcohol.

The extraction solvent may be particularly a $C_1$ to $C_3$ alcohol optionally in a mixture with water.

The term "$C_1$ to $C_3$ alcohol" denotes, according to the present invention, an alcohol R2OH wherein the chain R2 is a saturated, linear or branched hydrocarbon chain, comprising 1 to 3 carbon atoms. It may consist of methanol, ethanol, n-propanol or isopropanol, in particular methanol, ethanol or isopropanol. Preferably, it will be isopropanol.

The organic solvent not miscible with the oil obtained from *Silybum marianum* (L.) Gaertn. achenes, in particular a $C_1$ to $C_3$ alcohol such as methanol, ethanol or isopropanol, may be used in a mixture with water, particularly in a volume ratio of organic solvent/water between 80/20 and 100/0, particularly between 85/15 and 95/5, in particular approximately 90/10.

The extraction solvent may particularly be chosen from methanol, a methanol/water mixture, ethanol, an ethanol/water mixture, isopropanol and an isopropanol/water mixture.

According to a preferred embodiment, the extraction solvent will be methanol, an ethanol/water mixture in a volume ratio of approximately 90/10 or an isopropanol/water mixture in a volume ratio of approximately 90/10, preferably an isopropanol/water mixture in a volume ratio of approximately 90/10.

The step for extracting the oil obtained from *Silybum marianum* achenes will be performed in particular by mixing oil obtained from *Silybum marianum* achenes with the extraction solvent for 1 to 12 hrs and in particular at a temperature between 15 and 25° C., particularly approximately 20° C. The quantity of extraction solvent used to perform this extraction will be advantageously 0.5 to 3 g, in particular 1 to 3 g for 1 g of oil obtained from *Silybum marianum* (L.) Gaertn. achenes.

An extraction phase and a lipid phase will then be obtained at the end of this extraction. The extraction phase will be advantageously separated from the lipid phase and retrieved before being dried, partially or totally, particularly in a vacuum, to remove more or less the extraction solvent and obtain either the dry extract if the solvent is totally removed, or the concentrated extract which is diluted in residual solvent.

The oil obtained from *Silybum marianum* achenes may be advantageously obtained by extraction from *Silybum marianum* (L.) Gaertn. achenes (the achenes may be whole or in pieces), particularly by pressing, advantageously by cold pressing (i.e. without heating, at ambient temperature).

According to one embodiment according to the invention, the method according to the invention will comprise the following two successive steps:
 (i) extracting an oil from *Silybum marianum* (L.) Gaertn. achenes, and
 (ii) extracting the oil obtained from *Silybum marianum* (L.) Gaertn. achenes with an extraction solvent, comprising, particularly consisting of, a hydrotropic aqueous solution, subcritical water or an organic solvent not miscible with the oil obtained from *Silybum marianum* (L.) Gaertn. achene extract optionally in a mixture with water.

According to a preferred embodiment according to the invention, the method according to the invention will comprise the following successive steps:
(i) optionally extracting an oil from *Silybum marianum* (L.) Gaertn. achenes, and
(ii) extracting the oil obtained from *Silybum marianum* (L.) Gaertn. achenes with an extraction solvent, comprising, particularly consisting of, a hydrotropic aqueous solution, subcritical water or an organic solvent not miscible with the oil obtained from *Silybum marianum* (L.) Gaertn. achene extract optionally in a mixture with water,
(iii) retrieving the extraction phase obtained in step (ii), and
(iv) partially or totally drying the extraction phase to produce a concentrated or dry extract according to the invention.

Step (i) will be advantageously carried out by cold pressing *Silybum marianum* (L.) Gaertn. achenes, whole or in pieces. Step (ii) will be advantageously carried out with an extraction solvent as defined above, and particularly chosen from methanol, a methanol/water mixture, ethanol, an ethanol/water mixture, isopropanol and an isopropanol/water mixture.

The organic solvent not miscible with the oil obtained from *Silybum marianum* (L.) Gaertn. achenes, in particular a $C_1$ to $C_3$ alcohol such as methanol, ethanol or isopropanol, may be used in a mixture with water, particularly in a volume ratio of organic solvent/water between 80/20 and 100/0, particularly between 85/15 and 95/5, in particular approximately 90/10. An advantageous extraction solvent is an isopropanol/water mixture in a volume ratio of approximately 90/10.

The extraction step (ii) may be performed by mixing the oil obtained from *Silybum marianum* achenes with the extraction solvent for 1 to 12 hrs and in particular at a temperature between 15 and 25° C., particularly approximately 20° C. The quantity of extraction solvent used to perform this extraction will be advantageously 0.5 to 3 g, in particular 1 to 3 g for 1 g of oil obtained from *Silybum marianum* (L.) Gaertn. achenes. This extraction step (ii) makes it possible to obtain at the end an extraction phase of interest and a lipid phase.

Step (iii) will be performed advantageously by separating the extraction phase from the lipid phase.

Step (iv) will be advantageously performed in a vacuum.

Pharmaceutical or Cosmetic Composition According to the Invention

The pharmaceutical or cosmetic composition according to the invention comprises an extract according to the invention as defined above in a mixture with at least one pharmaceutically or cosmetically acceptable excipient. It preferably consists of a topical composition.

In the present invention, the term "pharmaceutically or cosmetically acceptable" denotes that which is usable in the preparation of a pharmaceutical or cosmetic composition, which is generally safe, non-toxic and neither biologically nor otherwise undesirable and which is acceptable for a pharmaceutical or cosmetic use, and in particular dermatological or dermo-cosmetic, particularly by topical application.

The compositions according to the invention are advantageously intended for topical application, in particularly on the skin.

The compositions according to the invention may thus be presented in the forms which are usually known for a topical administration, i.e. particularly lotions, foams, gels, dispersions, emulsions, sprays, serums, masks or creams, with excipients suitable particularly for skin penetration in order to enhance the properties and accessibility of the active ingredient. Advantageously, this will be a cream. These compositions generally contain, besides the extract according to the present invention, a physiologically acceptable medium, generally based on water or solvent, for example alcohols, ethers or glycols. They may also contain surfactants, complexing agents, preservatives, stabilisers, emulsifiers, thickeners, gelling agents, humectants, emollients, trace elements, essential oils, fragrances, colorants, mattifying agents, chemical or mineral filters, moisturising agents, mineral waters, etc.

According to one particular embodiment, the composition according to the present invention contains at least one pharmaceutically or cosmetically acceptable excipient selected from mattifying agents, moisturising agents, and mixtures thereof. According to another embodiment, the composition according to the present invention contains at least one mattifying agent and/or at least one moisturising agent, optionally with at least one chemical or mineral filter (UV filter).

A moisturising agent increases the moisture content of the skin and keeps it soft and smooth. It can be for example urea, an amino acid, glycerol (also called glycerin), propylene glycol, butylene glycol, sorbitol, xylitol, maltitol, mannitol, polydextrose, collagen, elastin, hyaluronic acid and its salts (such as sodium or potassium salts), pectin, gelatin, chitosan, aloe vera, honey, or a mixture thereof.

A mattifying agent is an ingredient that makes the skin matt, which prevents it from shining. It can be for example talc, silica, rice powder, or a mixture thereof, notably in a micronized form.

A UV filter is a compound that blocks or absorbs ultra-violet (UV) light in order to protect skin frum sun UVs notably. It can be for example a UVA filter, a UVB filter, a broad spectrum filter or a mixture thereof.

According to another particular embodiment, the composition according to the invention comprises, as pharmaceutically or cosmetically acceptable excipient, isopropanol, polyethyleneglycol (PEG) or a mixture thereof. As such, advantageously, the composition according to the present invention will comprise, particularly consist of, an extract according to the invention, isopropanol and polyethyleneglycol (PEG). The composition can also comprise an extract according to the invention, isopropanol, polyethyleneglycol (PEG) and at least one ingredient selected from mattifying agents, moisturising agents, UV filters and mixtures thereof. The composition can also comprise an extract according to the invention, isopropanol, polyethyleneglycol (PEG), at least one mattifying agent and/or at least another moisturising agent and optionally at least one chemical or mineral filter (UV filter). The mattifying agents, moisturising agents and UV filters are as defined above.

The mass ratio of isopropanol/PEG will be advantageously between 1/2 and 2/1, particularly between 1/1.5 and 1.5/1, in particular will be approximately 1/1.

The polyethyleneglycol may have in particular a mean molecular mass in number between 200 and 600 g/mol, particularly between 200 and 500 g/mol, in particular between 200 and 400 g/mol, for example between 250 and 350 g/mol, in particular approximately 300 g/mol. Thus, it may be in particular of PEG 300.

These compositions may further contain further active ingredients giving rise to a complementary or optionally synergistic effect.

Advantageously, the compositions according to the present invention will comprise at least 0.001% by weight, notably 0.001 to 15% by weight, 0.001 to 10% by weight or 0.001 to 5% by weight, in particular 0.01 to 15% by weight, 0.01 to 10% by weight or 0.01 to 5% by weight, preferably 0.1 to 10% by weight, notably 0.1 to 5% by weight, of an extract according to the invention with respect to the total volume of the composition.

Preferably, the composition according to the invention as defined above will not contain any vegetable oil, notably any oil.

Therapeutic Applications

The extracts according to the invention and the pharmaceutical compositions containing same are suitable for use in the treatment of acne (e.g. juvenile acne, also known as teenage acne, or adult acne, which may be cystic), seborrhoea, seborrheic dermatitis and/or rosacea, preferably by topical application, particularly on the skin.

FIGURES

Figure 4:
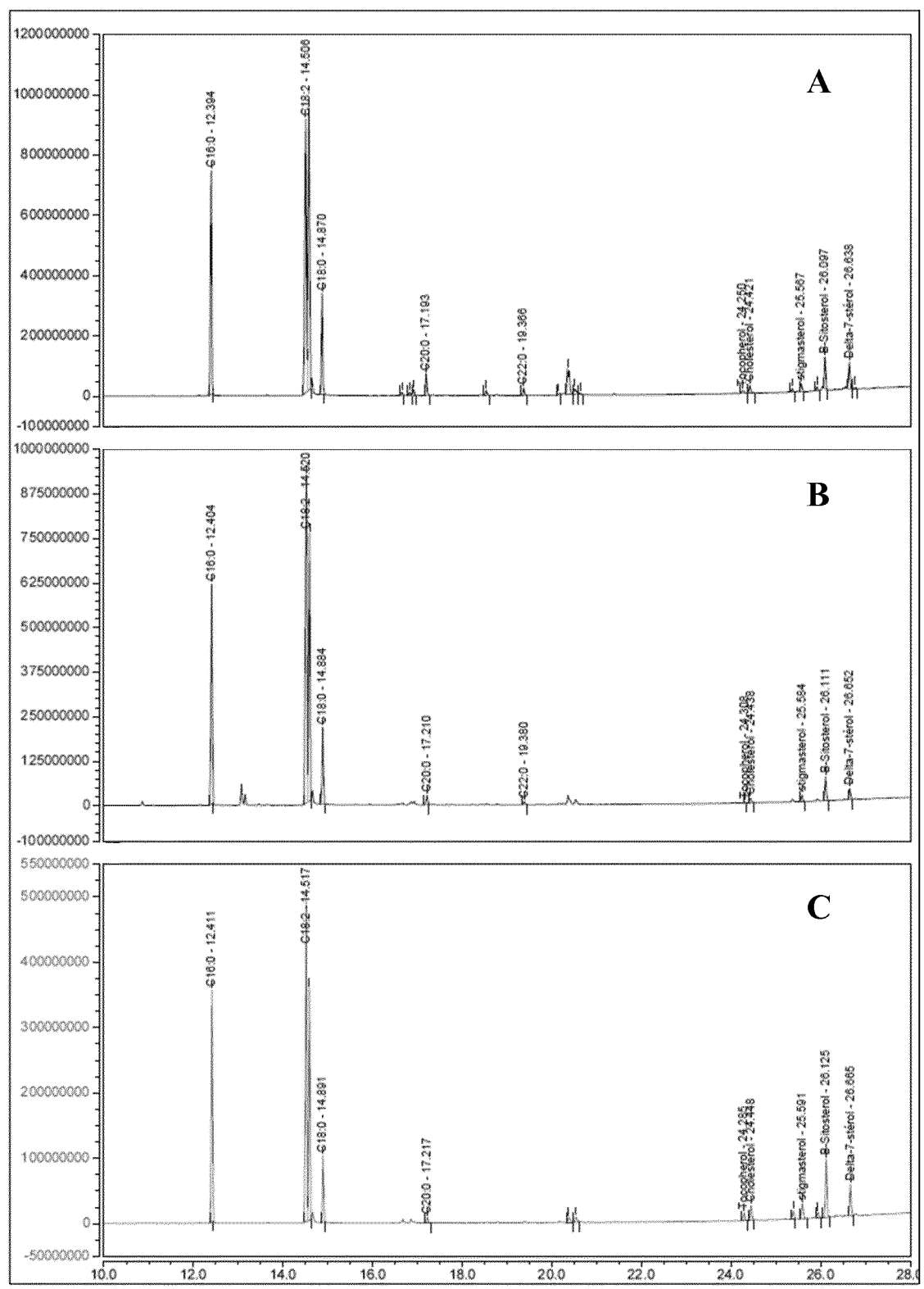

FIGS. 4A, 4B and 4C represent respectively the 10-28 min region (corresponding to the fatty acid and sterol region) of a GC-MS chromatogram of an ethanol 90 extract E according to the invention, of a methanol extract M according to the invention and of an isopropanol 90 extract I according to the invention obtained according to Protocol 3.

Figure 5:
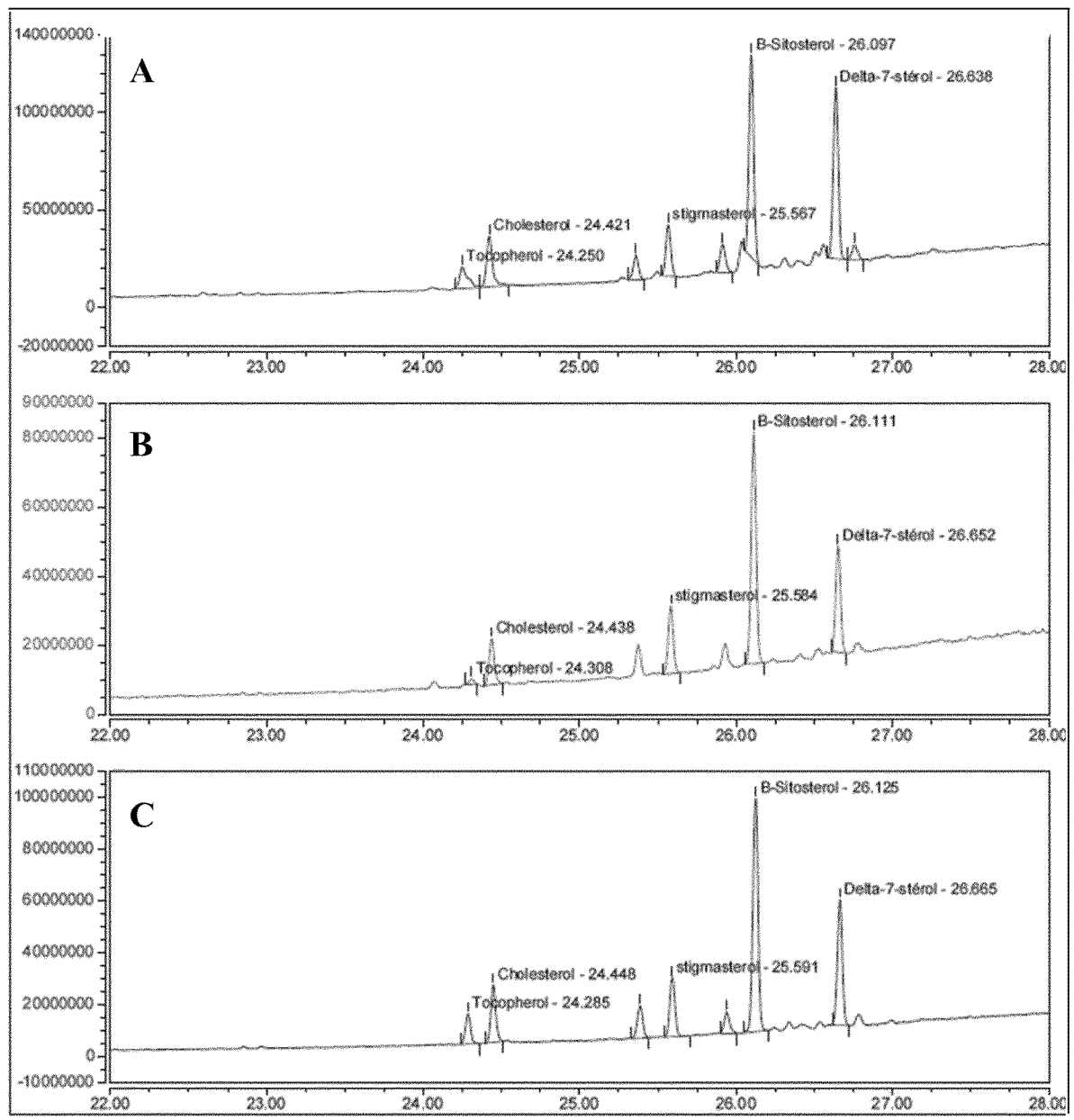

FIGS. 5A, 5B and 5C represent respectively the 22-28 min region (corresponding to the sterol region) of the chromatograms in FIGS. 4A, 4B and 4C.

Figure 6:
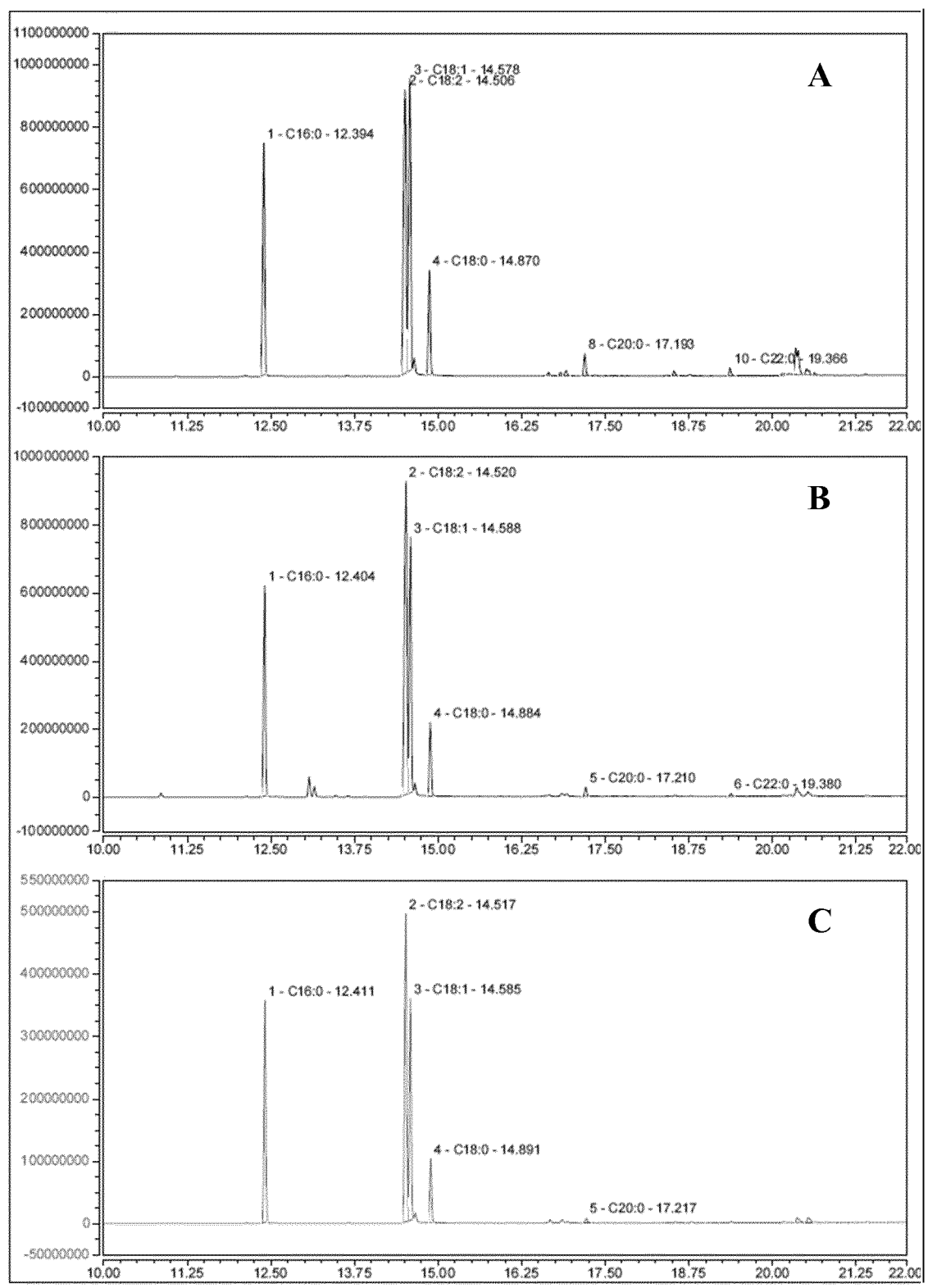

FIGS. 6A, 6B and 6C represent respectively the 10-22 min region (corresponding to the fatty acid region) of the chromatograms in FIGS. 4A, 4B and 4C.

Figure 7:
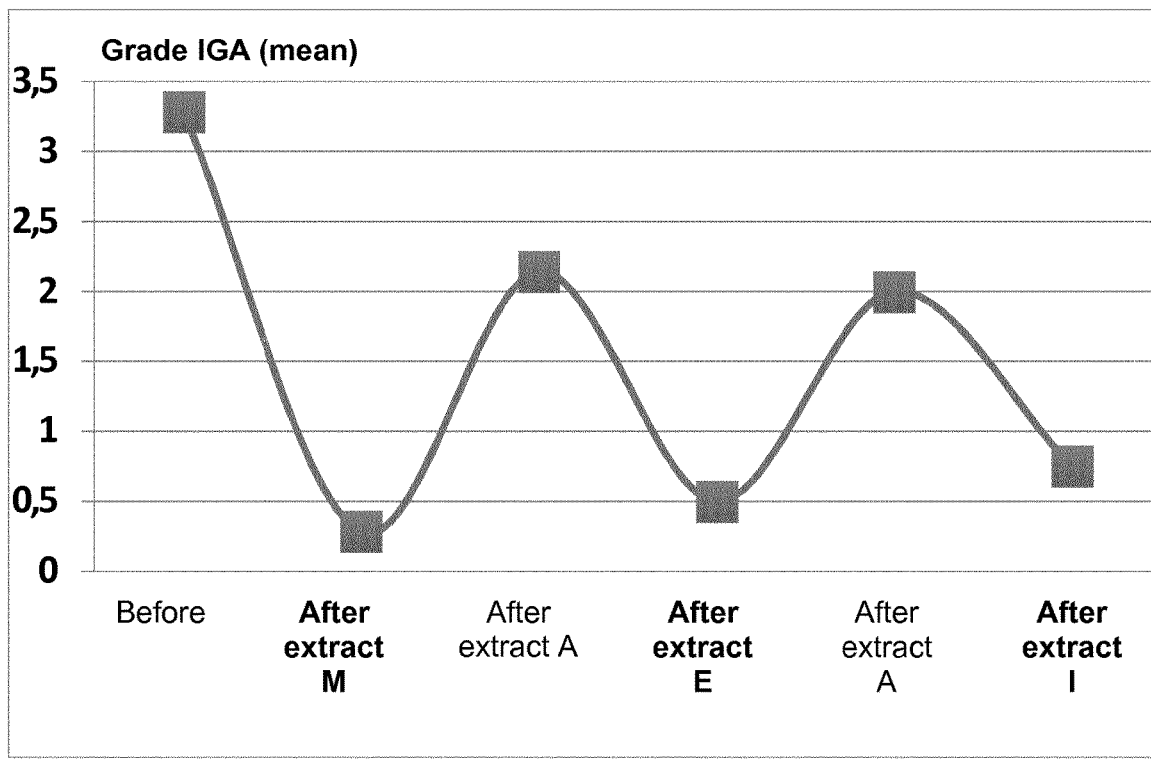

FIG. 7 shows the mean therapeutic effect on 7 patients suffering from acne determined by the IGA method after sequential treatment with *Silybum marianum* achene extracts according to the invention low in silymarin (extracts I, M and E) and *Silybum marianum* achene extracts according to the prior art rich in silymarin (extract A).

Figure 8:
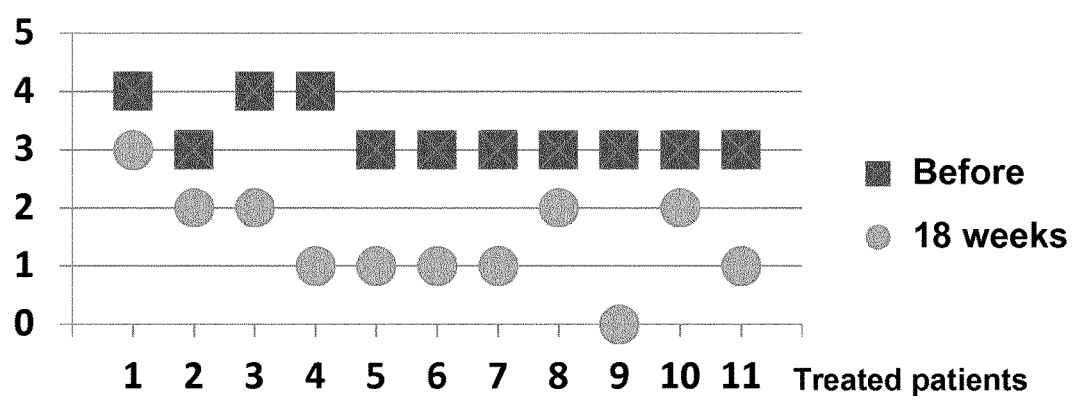

FIG. 8 shows the therapeutic effect of 11 patients suffering from adult acne determined by the IGA method after treatment with a *Silybum marianum* achene extract according to the invention.

Figure 9:
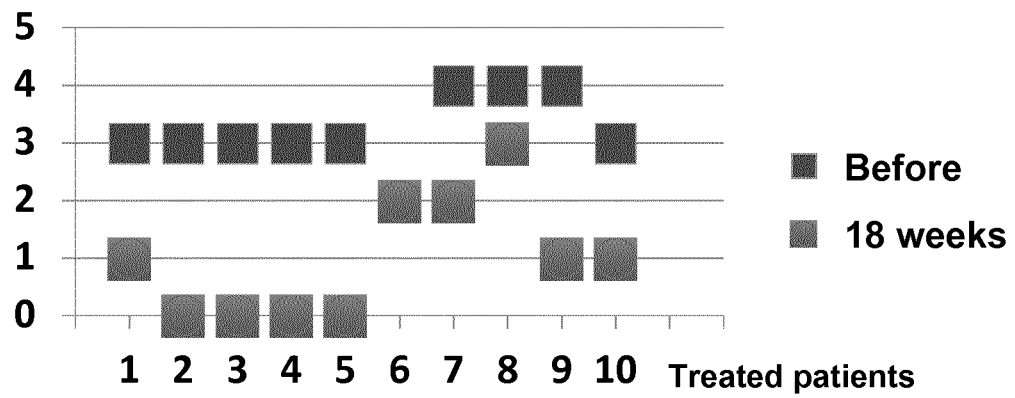

FIG. 9 shows the therapeutic effect of 10 patients suffering from teenage acne determined by the IGA method after treatment a *Silybum marianum* achene extract according to the invention.

Figure 10:
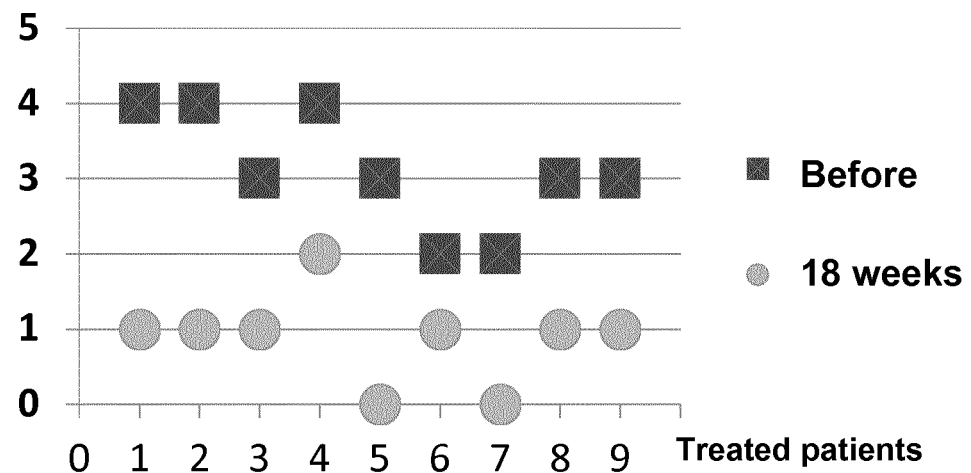

FIG. 10 shows the therapeutic effect of 9 patients suffering from rosacea with seborrhoea determined by the IGA method after treatment with a *Silybum marianum* achene extract according to the invention.

Figure 11:
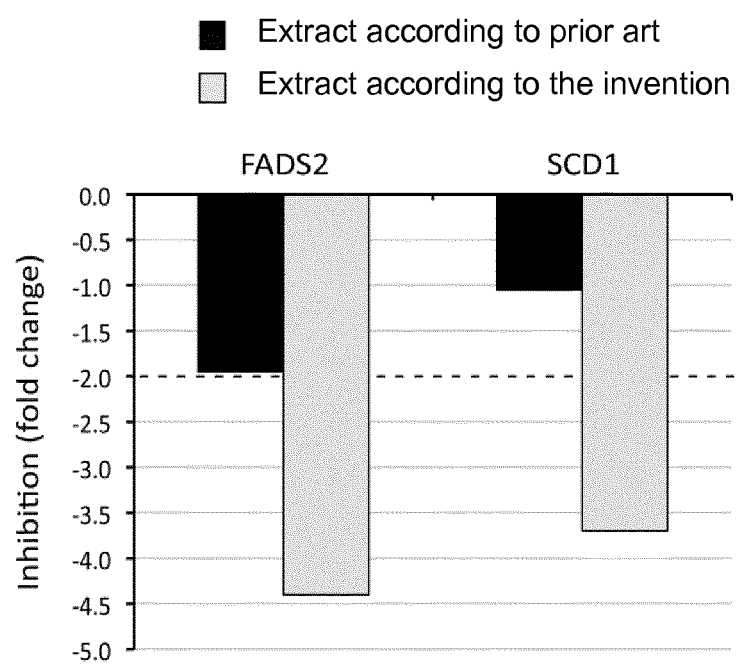

FIG. 11 represents the mean inhibition (fold) of two sebogenic enzyme genes FADS2 and SCD1 by a *Silybum marianum* achene extract according to the invention and a *Silybum marianum* achene extract according to the prior art.

EXAMPLES

1. Extract Preparation

Method A:

Method according to the prior art producing an extract A comprising a high silymarin content:
 extraction of *Silybum marianum* achenes with 96% ethanol for 1 hr at reflux with 10 ml of ethanol per gram of achenes,
 filtration of the mixture,
 retrieval of the ethanol phase, and
 evaporation of the solvent.

Method B:

Method according to the invention producing an isopropanol 90 extract (extract I) comprising a low silymarin content:
 cold pressing of *Silybum marianum* achenes to obtain an oil from *Silybum marianum* achenes,
 extraction of the oil obtained from *Silybum marianum* achenes with an isopropanol/water mixture (90/10 v/v) with 1 gram of the isopropanol/water mixture per gram of oil for 2 hours at 20° C.,
 retrieval of the isopropanol phase, and
 evaporation of the solvent.

Methanol (extract M) and ethanol 90 (extract E) extracts were obtained in a similar manner by replacing the isopropanol/water mixture (90/10 v/v) respectively by methanol and an ethanol/water mixture (90/10 v/v). The extraction of the oil obtained from *Silybum marianum* achenes is performed respectively with 3 volumes of methanol and with 3 volumes of the ethanol/water mixture (90/10 v/v) for 1 volume of oil for 2 hours at 20° C.

These different extracts were characterised by UPLC (ultra-high-performance liquid chromatography) or by GC-MS (gas chromatograph-mass spectrometry) according to the protocols detailed hereinafter.

Evaluation Protocols of the Obtained Extracts:

Protocol 1: Evaluation of Silymarin Content by UPLC

Sample and Standard Preparation:

Silymarin standard: Prepare a silymarin solution containing 5 mg in 10 ml of a methanol/water mixture (60:40) (v/v).

Sample:
 Extract A: Prepare a solution containing 100 mg of extract to be analysed in 10 ml of a methanol/dichloromethane mixture (70:30) (v/v)
 Extracts M, E, I: Heat the dry extract to be analysed to 35° C. under stirring until a clear, homogeneous solution is obtained. Accurately weigh 200 mg (pe) of the extract, solubilise it in 10 ml of a methanol/dichloromethane mixture enabling the total solubilisation of the extract and homogenise the solution. This mixture ranges from the ratio of methanol/dichloromethane (1:1) (v/v) to pure methanol.

Analytical Conditions:

Column: Acquity BEH Shield C18 150 mm×2.1 mm-1.7 μm (Waters)

Mobile phase:
 A: Water+0.1% formic acid
 B: Acetonitrile+0.1% formic acid

Gradient:

| T (min) | A (%) | B (%) |
|---------|-------|-------|
| 0 | 90 | 10 |
| 15 | 60 | 40 |
| 20 | 0 | 100 |
| 39.5 | 0 | 100 |
| 40 | 90 | 10 |
| 45 | 90 | 10 |

Column temperature: 40° C.
Flow rate: 0.4 ml/min
Detection: 287 nm
Injection volume: 1 µl
Protocol 2: Evaluation of Linoleic Acid Content by UPLC
Sample and Standard Preparation:
Linoleic acid standard: Prepare a linoleic acid solution containing 10 mg in 10 ml of a methanol/dichloromethane mixture (1:1) (v/v).
Sample:
  Extracts M, E, I: Heat the dry extract to be analysed to 35° C. under stirring until a clear, homogeneous solution is obtained. Accurately weigh 50 mg (pe) of the extract, solubilise it in 1 ml of a methanol/dichloromethane mixture enabling the total solubilisation of the extract and homogenise the solution. This mixture ranges from the ratio of methanol/dichloromethane (1:1) (v/v) to pure methanol.
Analytical Conditions:
Column: Acquity BEH Shield C18 150 mm×2.1 mm-1.7 µm (Waters)
Mobile phase:
  A: Water+0.1% formic acid
  B: Acetonitrile+0.1% formic acid
Gradient:

| T (min) | A (%) | B (%) |
|---------|-------|-------|
| 0 | 50 | 50 |
| 1 | 50 | 50 |
| 10 | 0 | 100 |
| 15 | 0 | 100 |
| 15.5 | 50 | 50 |
| 20 | 50 | 50 |

Column temperature: 40° C.
Flow rate: 0.4 ml/min
Detection: 215 nm
Injection volume: 1 µl
Protocol 3: Evaluation of Fatty Acid and Sterol Content by GC-MS
Sample Preparation:
Heat the dry extract to be analysed to 35° C. while stirring until a clear, homogeneous liquid is obtained
Solubilise 20 mg of the extract in 800 µL of a methanol/dichloromethane mixture (1:1) (v/v)
Add 200 µL of the derivatising agent N,O-Bis(trimethylsilyl)trifluoroacetamide (BSTFA)+Trimethylchlorosilane (TMCS) (99:1) (Supelco-Sigma Aldrich)
Stir for 1 minute with a vortex
Gas Chromatography (GC) Conditions
Column: DB-5 ms (Agilent technologies); 30 m×0.25 mm; 0.25 µm
Injection: T=300° C.; Mode=Split; Split ratio=100:1
Oven: Temperature gradient (° C.):
  Initial temperature=150° C.
  Gradient=7° C./min up to Final temperature=340° C.
  Maintain at 340° C. for 10 minutes
Carrier gas flow rate: 1 ml/min
Detection: MS-EI; T=300° C.; Scan Time=0.2 sec.; Full Scan Start Mass=40; Full Scan End Mass=600
Injection volume: 1 µl
Results:
The *Silybum marianum* achene extract A according to the prior art rich in silymarin essentially contains the constituents of silymarin having retention times between 6 and 14 minutes by UPLC (see FIGS. 1C and 1A).

The *Silybum marianum* achene extract I according to the invention low in silymarin contains mostly substances having a retention time between 13 and 30 minutes by UPLC (see FIG. 1B).

Method A thus favours the extraction of polar compounds, and in particular silymarin flavonolignans, whereas method B favours the extraction of lipophilic compounds such as free fatty acids, sterols, tocopherols and other apolar compounds.

Figure 1:
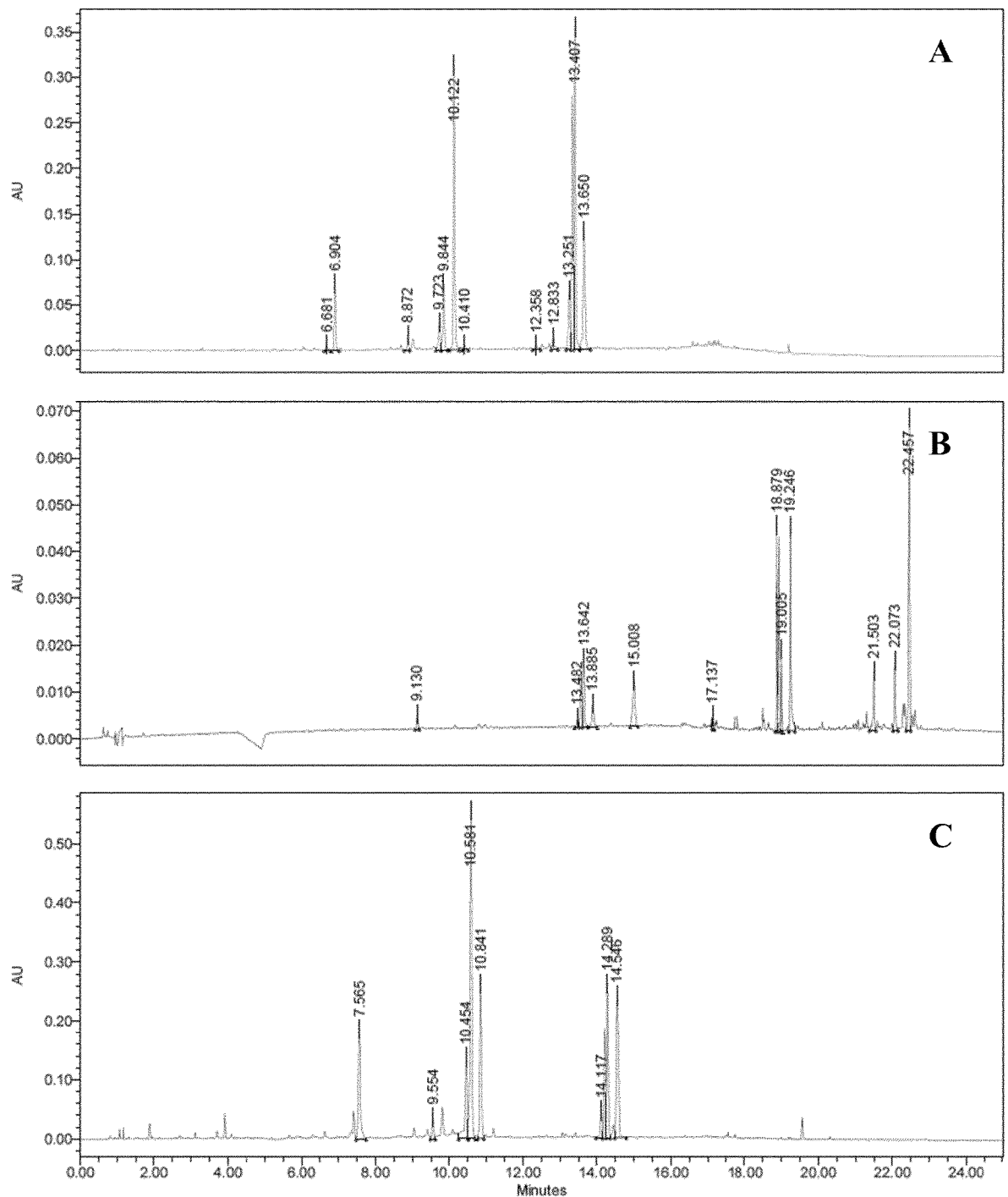
FIGS. 1A, 1B and 1C represent respectively a UPLC chromatogram of silymarin (Sigma Aldrich), of a *Silybum marianum* achene extract I according to the invention and of a *Silybum marianum* achene extract A according to the prior art obtained according to Protocol 1.

The silymarin content of extracts A and I was determined by UPLC after calibration with standard commercial silymarin solutions (Sigma Aldrich) (see FIG. 1).
  Extract A contains 28% by mass of silymarin.
  Extract I contains 0.06% by mass of silymarin.

Figure 3:
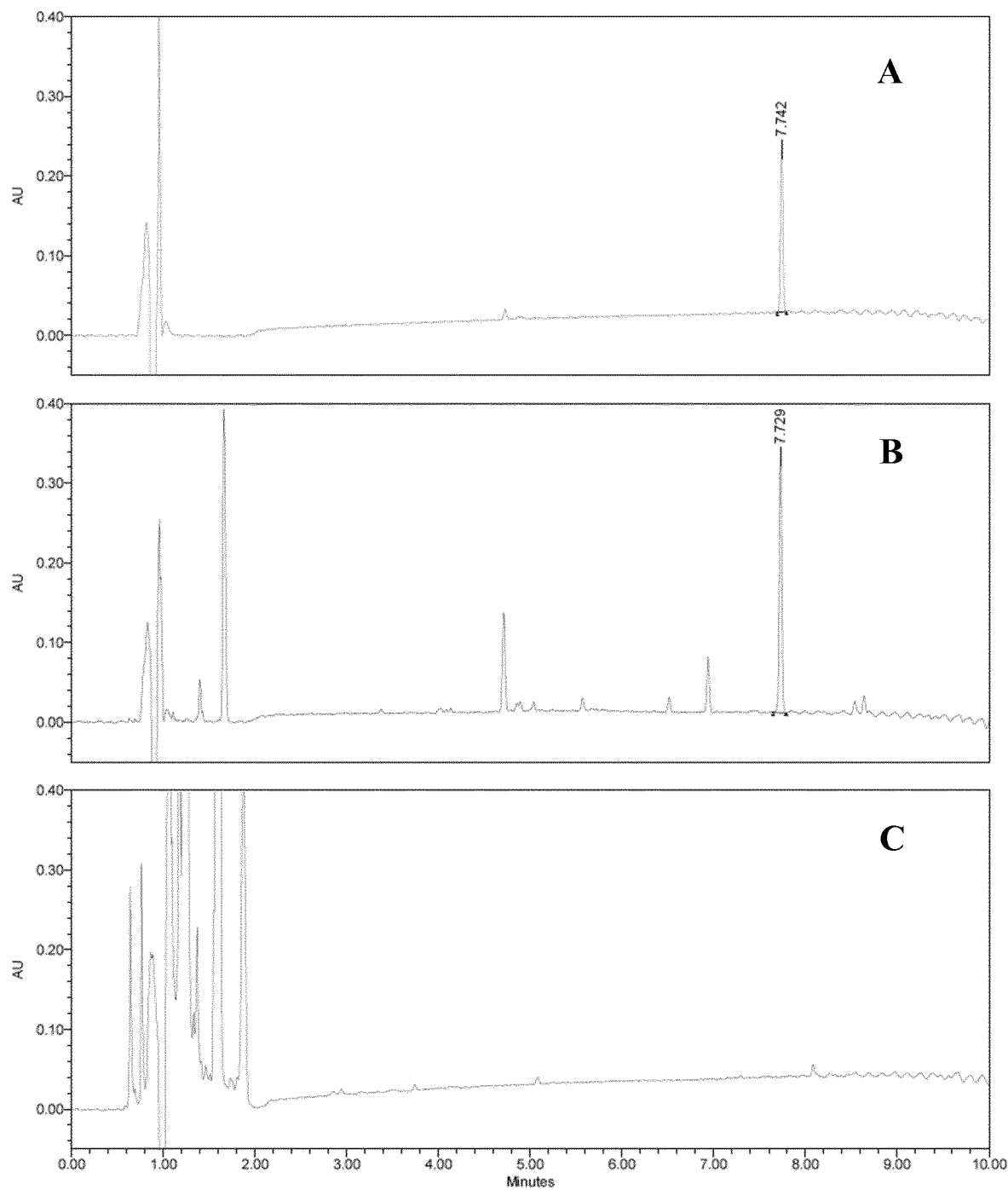
FIGS. 3A, 3B and 3C represent respectively a UPLC chromatogram of linoleic acid, of a *Silybum marianum* achene extract I according to the invention and of a *Silybum marianum* achene extract A according to the prior art obtained according to Protocol 2.

The free fatty acid (and more particularly linoleic acid) and sterol (and more particularly β-sitosterol) contents in extract I were determined by UPLC (see FIG. 3B) and by GC (see FIGS. 4C, 5C and 6C):

| Compounds | % by weight |
|-----------|-------------|
| Free fatty acids (essentially palmitic, oleic and linoleic acids) | 24.6 |
| of which linoleic | 5.1 |
| Sterols | 3.6 |
| of which beta-sisterol | 1.5 |

Figure 2:
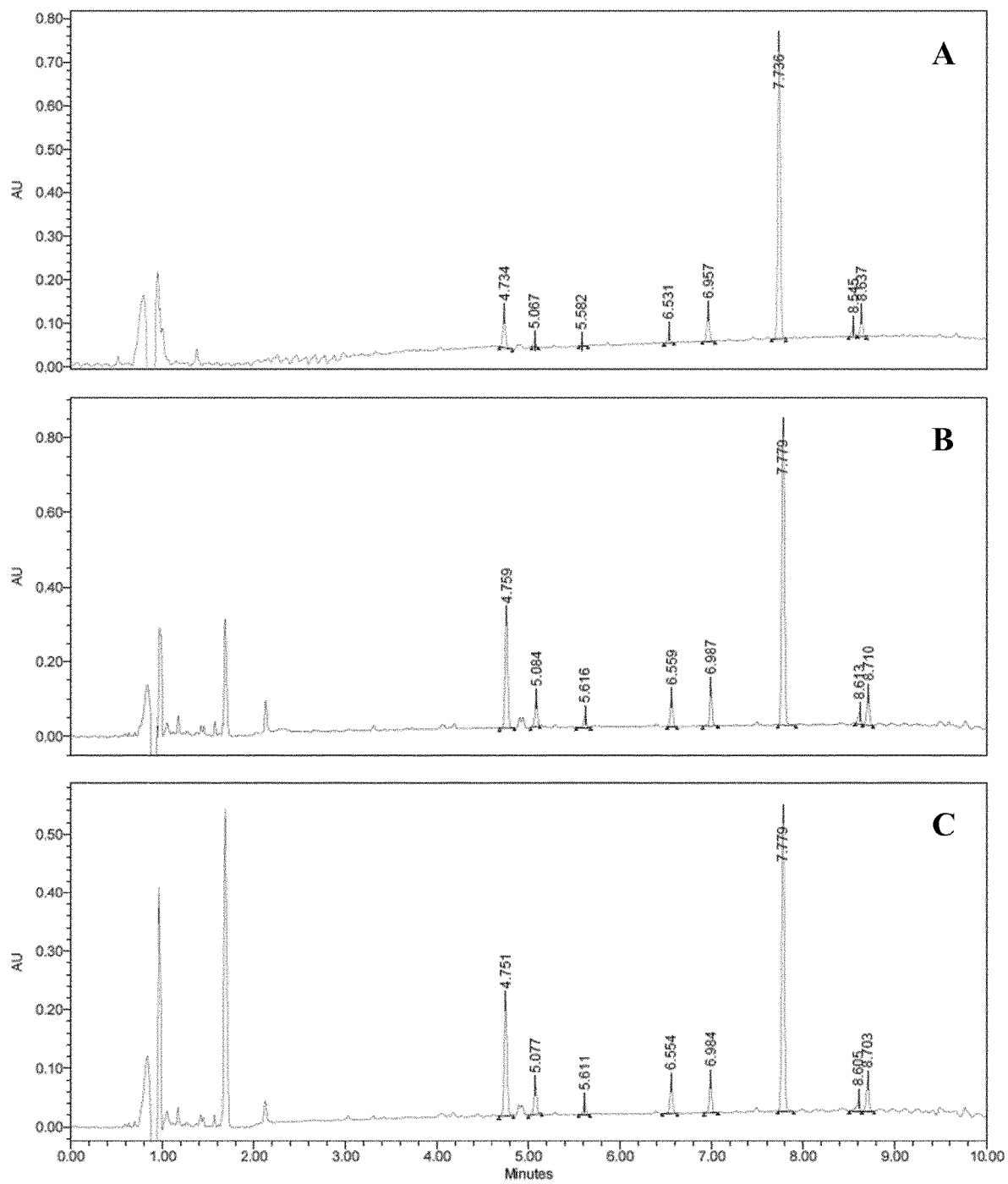
FIGS. 2A, 2B and 2C represent respectively a UPLC chromatogram of a methanol extract M according to the invention, of an ethanol 90 extract E according to the invention and of an isopropanol 90 extract I according to the invention obtained according to Protocol 2.

We were able to determine that the UPLC (see FIG. 2) and GC (see FIGS. 4, 5 and 6) of the 3 achene extracts according to the invention obtained by methanol extraction (extract M), ethanol 90 extraction (extract E) and isopropanol 90 extraction (extract I) are similar.

Conclusion:
The various analyses performed by UPLC and GC-MS made it possible to demonstrate the following characteristics.
  "Silymarin chromatograms" (see FIG. 1): The comparison of these chromatograms demonstrates that:
    the isopropanol 90 achene extract according to the invention (extract I) contains practically no silymarin, particularly polar flavolignans;
    the ethanol extract according to the prior art (extract A) is for its part rich in silymarin. It is titrated as 28% by mass of silymarin.
  "Linoleic acid chromatogram" (see FIG. 3): linoleic acid is the peak at 7.742 min. It is noted that the ethanol achene extract according to the prior art (extract A) is practically devoid of linoleic acid, unlike the isopropanol 90 extract according to the invention (extract I).
  Moreover, we were also able to demonstrate that the UPLC (see FIG. 2) and GC (see FIGS. 4, 5 and 6) profiles of the 3 achene extracts according to the invention obtained by methanol, ethanol 90 and isopropanol 90 extraction (extracts M, E and I) are very similar.

2. Compositions According to the Invention

The extracts prepared in example 1 were formulated at 7% (w/v) in an isopropanol/PEG 300 mixture (1:1) (w/w). The resulting compositions were used in various clinical studies (see examples 3 to 6 hereinafter) by topical application on the skin.

The extracts according to the present invention can also be formulated for example in the form of a serum according to the following formulation:

| Ingredient | Quantity (% w/w) |
| --- | --- |
| *Silybum marianum* achene extract | 0.01-5% |
| Polyacrylate-13 | 0.3-2% |
| Glycerin (moisturising agent) | 1-15% |
| Silica (mattifying agent) | 0.1-1% |
| Carrier: Isopropanol/PEG 300 mixture (1:1) and Thermal water | Qsp |

3. Comparative Clinical Study in the Treatment of Acne

Seven patients suffering from acne were treated sequentially with compositions from example 2 comprising a *Silybum marianum* achene extract according to the invention low in silymarin (extract I, M or E) or a *Silybum marianum* achene extract according to the prior art rich in silymarin (extract A), according to the following schedule:
- phase 1: 18-week treatment with a composition containing a *Silybum marianum* achene extract M according to the invention low in silymarin (5.64±0.01 µg/g), followed by
- phase 2: 12-week treatment with a composition containing a *Silybum marianum* achene extract A according to the prior art rich in silymarin (23.21±2.03 mg/g), followed by
- phase 3: 18-week treatment with a composition containing a *Silybum marianum* achene extract E according to the invention low in silymarin, followed by
- phase 4: 6-week treatment with a composition containing a *Silybum marianum* achene extract A according to the prior art rich in silymarin, followed by
- phase 5: 6-week treatment with a composition containing a *Silybum marianum* achene extract I according to the invention low in silymarin.

The analysis of the therapeutic effects obtained was performed according to the global clinical status analysis method IGA (Investigator Global Assessment) accepted by the FDA (Food and Drug Administration) and applied by a clinical dermatology expert (Guidance for Industry Acne Vulgaris: Developing Drugs for Treatment).

With such a method, the following IGA grades are assigned according to the severity of the acne observed:

| IGA grade | Patient status |
| --- | --- |
| 0 | Clear skin with no inflammatory or noninflammatory lesions |
| 1 | Almost clear; rare noninflammatory lesions with no more than one small inflammatory lesion |
| 2 | Mild severity; greater than Grade 1; some noninflammatory lesions with no more than a few inflammatory lesions (papules/pustules only, no nodular lesions) |
| 3 | Moderate severity; greater than Grade 2; up to many noninflammatory lesions and may have some inflammatory lesions, but no more than one small nodular lesion |
| 4 | Severe; greater than Grade 3; up to many noninflammatory and inflammatory lesions, but no more than a few nodular lesions |

The mean results obtained for the seven patients are shown in FIG. 7.

This figure shows that, during the first treatment phase with *Silybum marianum* achene extract according to the invention low in silymarin, a notable improvement in the clinical status of acne is observed, corresponding to a "success" according to FDA criteria, with a notable stability of the effect in the light of the exceptional duration (18 weeks) of treatment.

Upon the transition to the second treatment phase with a *Silybum marianum* achene extract according to the prior art rich in silymarin, a loss of efficacy is observed with a return of lesions, corresponding to a "failure" according to FDA criteria.

The same observations were made during the subsequent phases 3, 4 and 5.

These clinical observations clearly indicate that the clinical therapeutic effect observed is not associated with silymarin since the compositions containing infinitesimal silymarin concentrations exert a notable clinical therapeutic effect whereas the compositions containing high silymarin concentrations tend to worsen the clinical status, causing a relapse.

Thus, a treatment with a *Silybum marianum* achene extract according to the prior art rich in silymarin causes a degradation of the clinical status, whereas a treatment with a *Silybum marianum* achene extract according to the invention low in silymarin provides a marked improvement.

The clinical results observed therefore demonstrate that the efficacy is superior with the extracts according to the invention containing a negligible quantity of silymarin compared to the extracts according to the prior art rich in silymarin which result in a resumption of acne.

4. Clinical Study in the Treatment of Adult Acne

Eleven patients suffering from adult acne were treated for 18 weeks with a composition from example 2 comprising a *Silybum marianum* achene extract according to the invention low in silymarin.

The analysis of the therapeutic effects obtained was performed as in example 3 according to the global clinical status analysis method IGA (Investigator Global Assessment) accepted by the FDA (Food and Drug Administration) and applied by a clinical dermatology expert (Guidance for Industry Acne Vulgaris: Developing Drugs for Treatment).

The results obtained are shown in FIG. 8 and in the table below:

| | | IGA grade | |
| --- | --- | --- | --- |
| Patients | Status severity | Before treatment | After treatment |
| Male suffering from adult acne (post-Curacne) | severe | 4 | 3 |

-continued

| Patients | Status severity | IGA grade Before treatment | IGA grade After treatment |
|---|---|---|---|
| Male suffering from cystic adult acne | severe | 3 | 2 |
| Female suffering from adult acne | severe | 4 | 2 |
| Female suffering from adult acne | severe | 4 | 1 |
| Female suffering from adult acne | severe | 3 | 1 |
| Female suffering from adult acne | moderate | 3 | 1 |
| Female suffering from adult acne | moderate | 3 | 1 |
| Female suffering from adult acne and from polycystic ovary syndrome (PCOS) | moderate | 3 | 2 |
| Female suffering from adult acne | moderate | 3 | 0 |
| Female suffering from adult acne | moderate | 3 | 2 |
| Female suffering from adult acne | moderate | 3 | 1 |
| TOTAL | | 36 | 16 |
| MEAN | | 3.27 | 1.45 |

These results demonstrate a notable improvement in the clinical status of adult acne, with a decrease by two grades in 7 out of 11 cases corresponding to a "success" according to FDA criteria, as well as notable stability of the effect in the light of the exceptional duration (18 weeks) of treatment.

These clinical observations demonstrate an indisputable clinical therapeutic effect of an extract according to the invention on adult acne.

5. Clinical Study in the Treatment of Teenage Acne

Ten teenage patients (15-18 years) suffering from teenage acne were treated for 18 weeks with a composition from example 2 comprising a *Silybum marianum* achene extract according to the invention low in silymarin.

The analysis of the therapeutic effects obtained was performed as in example 3 according to the global clinical status analysis method IGA (Investigator Global Assessment) accepted by the FDA (Food and Drug Administration) and applied by a clinical dermatology expert (Guidance for Industry Acne Vulgaris: Developing Drugs for Treatment).

The results obtained are shown in FIG. 9 and in the table below:

| Patients | Status severity | IGA grade Before treatment | IGA grade After treatment |
|---|---|---|---|
| Male suffering from teenage acne | moderate | 3 | 1 |
| Male suffering from teenage acne | moderate | 3 | 0 |
| Female suffering from teenage acne | moderate | 3 | 0 |
| Female suffering from teenage acne | moderate | 3 | 0 |
| Female suffering from teenage acne | moderate | 3 | 0 |
| Male suffering from acne naevus | moderate | 2 | 2 |
| Male suffering from teenage acne | severe | 4 | 2 |
| Female suffering from teenage acne | severe | 4 | 3 |
| Female suffering from teenage acne | severe | 4 | 1 |
| Female suffering from teenage acne | severe | 4 | 1 |
| TOTAL | | 33 | 10 |
| MEAN | | 3.30 | 1.00 |

These results demonstrate a notable improvement in the clinical status of teenage acne, with a decrease by two grades in 8 out of 10 cases corresponding to a "success" according to FDA criteria, as well as notable stability of the effect in the light of the exceptional duration (18 weeks) of treatment.

These clinical observations demonstrate an indisputable clinical therapeutic effect of an extract according to the invention on teenage acne.

6. Clinical Study in the Treatment of Rosacea, Optionally with Seborrhoea

Nine patients suffering from rosacea, optionally with seborrhoea, were treated for 18 weeks with a composition from example 2 comprising a *Silybum marianum* achene extract according to the invention low in silymarin.

The analysis of the therapeutic effects obtained was performed as in example 3 according to the global clinical status analysis method IGA (Investigator Global Assessment) accepted by the FDA (Food and Drug Administration) for acne and adapted to rosacea by a clinical dermatology expert (Guidance for Industry Acne Vulgaris: Developing Drugs for Treatment).

The results obtained are shown in FIG. 10 and in the table below:

| Patients | Status severity | IGA grade Before treatment | IGA grade After treatment |
|---|---|---|---|
| Male suffering from rosacea and seborrheic dermatitis (post-Curacne) | severe | 4 | 1 |
| Female suffering from rosacea and seborrheic dermatitis (post-Curacne) | severe | 4 | 1 |
| Female suffering from rosacea fulminans (post-Curacne) | severe | 3 | 1 |
| Female suffering from rosacea | severe | 4 | 2 |
| Female suffering from rosacea | moderate | 3 | 0 |
| Female suffering from rosacea on oral steroids | moderate | 2 | 1 |
| Male suffering from rosacea and seborrheic dermatitis | moderate | 2 | 0 |

-continued

| Patients | Status severity | IGA grade Before treatment | After treatment |
|---|---|---|---|
| Male suffering from rosacea and seborrheic dermatitis | moderate | 3 | 1 |
| Female suffering from rosacea and seborrheic dermatitis | moderate | 3 | 1 |
| TOTAL | | 28 | 8 |
| MEAN | | 3.11 | 0.89 |

These results demonstrate a notable improvement of the clinical status of rosacea for all patients, as well as notable stability of the effect in the light of the exceptional duration (18 weeks) of treatment. This global improvement corresponds to a notable effect on the various clinical parameters of this condition (Wilkin et al. 2004): vascular, inflammatory, papulopustular component, and furthermore on the seborrheic components, embodying in these cases seborrheic dermatitis (SD) of the "mixed facial dermatitis" type. This seborrheic dermatitis associates rosacea lesions in the typical areas of this condition, i.e. the convexities of the face, and seborrheic dermatitis lesions in fold areas as described by B. Cribier in Traité Francophone de Dermatologie 5$^{th}$ edition (Cribier B. Dermatoses faciales page 861 in Dermatologie et IST, 5$^{th}$ edition Elsevier Masson 2009).

These clinical observations demonstrate an indisputable clinical therapeutic effect of an extract according to the invention on rosacea, optionally with seborrhoea.

7. In Vitro Comparative Study

In this study, isopropanol *Silybum marianum* achene extracts at a concentration of 0.03% (w/v) in culture medium were tested in vitro on a primary human sebocyte culture (Zenbio, Inc. Research Triangle Park, N.C.) for 3 consecutive days (with replacement of the medium each day), i.e. a *Silybum marianum* achene extract according to the invention and a *Silybum marianum* achene extract A according to the prior art. The cells were harvested and the RNA extracted 24 hrs after the final treatment.

A PCR (polymerase chain reaction) analysis made it possible to measure the level of expression of two sebogenic enzyme genes FADS2 and SCD1. These two enzymes are involved in the synthesis of the specific lipids of sebum, and it is known that the inhibition thereof induces a decrease in sebaceous gland activity. The mean inhibition results (fold change) of these two genes with respect to the solvent (isopropanol of which the concentration in the culture medium is 1%) obtained from at least 5 experiments are shown in FIG. 11, a 2-fold inhibition being considered to be significant.

These results thus demonstrate that a *Silybum marianum* achene extract according to the invention low in silymarin significantly inhibits the expression of these two genes, unlike a *Silybum marianum* achene extract according to the prior art rich in silymarin.

BIBLIOGRAPHIC REFERENCES

Berardesca et al. "Combined effects of silymarin and methylsulfonylmethane in the management of rosacea: clinical and instrumental evaluation" *Journal of Cosmetic Dermatology* 2008, 7, 8-14 Cribier B. Dermatoses faciales page 861 in Dermatologie et IST, 5th edition Elsevier Masson 2009

"Guidance for Industry Acne Vulgaris: Developing Drugs for Treatment" Draft guidance, U.S. Department of Health and Human Services Food and Drug Administration Center for Drug Evaluation and Research (CDER), September 2005.

Hermenean et al. "Antioxidant and hepatoprotective activity of milk thistle (*Silybum marianum* L. Gaertn.) seed oil" *Open Life Sci.* 2015, 10(1), 225-236.

Kuki et al. "Identification of Silymarin Consituents: An Improved HPLC-MS Method" *Chromatographia* 2012, 75:175-180.

Sahib et al. "Effects of Oral Antioxidants on Lesion Counts Associated with Oxidative Stress and Inflammation in Patients with Papulopustular Acne" *J. Clin. Exp. Dermatol. Res.* 2012, 3:5.

Wilkin et al. "Standard grading system for rosacea: Report of the National Rosacea Society Expert Committee on the Classification and Staging of Rosacea" *J. Am. Acad. Dermatol.* 2004, 50:907-12.

Zheng et al. "Application of response surface methodology to optimize microwave-assisted extraction of silymarin from milk thistle seeds" *Sep. Purif. Technol.* 2009, 70:34-40.

Zhu et al. "*Silybum marianum* oil attenuates oxidative stress and ameliorates mitochondrial dysfunction in mice treated with D-galactose" Pharmacogn Mag. 2014, 10 (Suppl. 1), S92-S99.

The invention claimed is:

1. A method for treating acne, seborrhoea, rosacea and/or seborrheic dermatitis comprising administering to a subject in need thereof of an effective quantity of a *Silybum marianum* (L.) Gaertn. achene extract comprising less than 0.2% by weight of silymarin with respect to the weight of a dry extract of the *Silybum marianum* (L.) Gaertn. achene extract,
   wherein the extract is obtainable by a method comprising a step for extracting an oil obtained from *Silybum marianum* (L.) Gaertn. achenes with an extraction solvent comprising a hydrotropic aqueous solution, subcritical water or an organic solvent not miscible with the oil obtained from *Silybum marianum* (L.) Gaertn. achenes optionally in a mixture with water.

2. The method according to claim 1, wherein the extract contains between 0.5% and 2.5% by weight of beta-sitosterol with respect to the weight of the dry extract.

3. The method according to claim 2, wherein the mass ratio of silymarin/beta-sitosterol in the extract is less than 0.4 and the extract contains between 2 and 7% by weight of sterols with respect to the weight of the dry extract.

4. The method according to claim 1, wherein the extract contains between 3% and 15% by weight of free linoleic acid with respect to the weight of the dry extract.

5. The method according to claim 4, wherein the extract contains between 10% and 50% by weight of free fatty acids with respect to the weight of the dry extract.

6. The method according to claim 1, wherein the extract contains between 0.01% and 0.5% by weight of tocopherols with respect to the weight of the dry extract.

7. The method according to claim 1, wherein the extract is a dry extract.

8. The method according to claim 1, wherein the extract is obtainable by a method comprising the following successive steps:
   (i) optionally extracting an oil from *Silybum marianum* (L.) Gaertn. achenes, (ii) extracting the oil obtained from *Silybum marianum* (L.) Gaertn. achenes with the extraction solvent to obtain an extraction phase and a lipid phase, (iii) retrieving the extraction phase obtained in step (ii), and (iv) partially or totally drying the extraction phase to produce a concentrated or dry extract.

9. The method according to claim 8, wherein the step (i) is carried out by pressing *Silybum marianum* (L.) Gaertn. achenes.

10. The method according to claim 1, wherein the organic solvent not miscible with the oil obtained from *Silybum marianum* (L.) Gaertn. achenes is selected from the group consisting of methanol, ethanol, isopropanol, and mixtures thereof.

11. The method according to claim 1, wherein the extraction solvent is an isopropanol/water mixture in a volume ratio of approximately 90/10.

12. A method for treating acne, seborrhoea, rosacea and/or seborrheic dermatitis comprising administering to a subject in need thereof of an effective quantity of a pharmaceutical or cosmetic composition comprising a *Silybum marianum* (L.) Gaertn. achene extract in a mixture with at least one pharmaceutically or cosmetically acceptable excipient, wherein the *Silybum marianum* (L.) Gaertn. achene extract comprises less than 0.2% by weight of silymarin with respect to the weight of a dry extract of the *Silybum marianum* (L.) Gaertn. achene extract, wherein the extract is obtainable by a method comprising a step for extracting an oil obtained from *Silybum marianum* (L.) Gaertn. achenes with an extraction solvent comprising a hydrotropic aqueous solution, subcritical water or an organic solvent not miscible with the oil obtained from *Silybum marianum* (L.) Gaertn. achenes optionally in a mixture with water.

13. The method according to claim 12, wherein the pharmaceutical or cosmetic composition is topically administered.

14. The method according to claim 12, wherein the pharmaceutical or cosmetic composition further comprises isopropanol and polyethyleneglycol (PEG).

15. The method according to claim 12, wherein the pharmaceutical or cosmetic composition comprises 0.001 to 15% by weight of the *Silybum marianum* (L.) Gaertn. achene extract with respect to the total volume of the composition.

* * * * *